United States Patent
Wu et al.

(10) Patent No.: US 9,500,575 B2
(45) Date of Patent: Nov. 22, 2016

(54) FULL-AUTOMATIC DYNAMIC TOBACCO MOISTURE ANALYSIS CLIMATE CHAMBER

(71) Applicant: SHANGHAI TOBACCO GROUP CO., LTD, Shanghai (CN)

(72) Inventors: Da Wu, Shanghai (CN); Yunfei Sha, Shanghai (CN); Jiaying Lou, Shanghai (CN); Bing Wang, Shanghai (CN); Baizhan Liu, Shanghai (CN)

(73) Assignee: SHANGHAI TOBACCO GROUP CO., LTD, Yangpu District, Shanghai (CN)

( * ) Notice: Subject to any disclaimer, the term of this patent is extended or adjusted under 35 U.S.C. 154(b) by 0 days.

(21) Appl. No.: 15/024,837

(22) PCT Filed: Aug. 18, 2014

(86) PCT No.: PCT/CN2014/084596
§ 371 (c)(1),
(2) Date: Mar. 24, 2016

(87) PCT Pub. No.: WO2015/043332
PCT Pub. Date: Apr. 2, 2015

(65) Prior Publication Data
US 2016/0216186 A1 Jul. 28, 2016

(30) Foreign Application Priority Data
Sep. 25, 2013 (CN) .......................... 2013 1 0442801

(51) Int. Cl.
*G01G 7/00* (2006.01)
*G01N 5/04* (2006.01)

(52) U.S. Cl.
CPC ............... *G01N 5/045* (2013.01); *G01G 7/00* (2013.01)

(58) Field of Classification Search
CPC .............................. G01G 7/00; G01N 5/045
USPC ........................................................... 73/73
See application file for complete search history.

(56) References Cited

U.S. PATENT DOCUMENTS

| 5,404,919 A * | 4/1995 | Felts ......................... A24B 1/10 100/215 |
| 6,158,440 A * | 12/2000 | Uematsu ................ A24B 3/185 131/291 |
| 2013/0192340 A1* | 8/2013 | Liu ...................... G01N 30/461 73/23.39 |

FOREIGN PATENT DOCUMENTS

| CN | 2096064 U | 2/1992 |
| CN | 200983827 Y * | 12/2007 |
| CN | 201397263 Y | 2/2010 |

(Continued)

*Primary Examiner* — Lisa Caputo
*Assistant Examiner* — Jamel Williams
(74) *Attorney, Agent, or Firm* — Global IP Services; Tianhua Gu

(57) ABSTRACT

A full-automatic dynamic tobacco moisture analysis climate chamber comprises an enclosed constant-temperature constant-humidity cabin, which is communicated with an air temperature and humidity processor to form an air circulation loop; a weighing platform is disposed inside the constant-temperature constant-humidity cabin, a sample delivery hanger is hung inside the constant-temperature constant-humidity cabin, at least one placement carrier is disposed below the sample delivery hanger, a sample vessel is placed on the placement carrier, the sample delivery hanger is further connected to a drive mechanism outside the constant-temperature constant-humidity cabin and the drive mechanism drives the sample delivery hanger to perform operations, to place the sample vessel on the weighing platform for weighing. The climate chamber, can minimize the test period, minimize intermediate links and human operation errors, and obtain a moisture content change rule of a tobacco sample as an important basis for performance evaluation of a tobacco humectant.

8 Claims, 1 Drawing Sheet

(56) References Cited

FOREIGN PATENT DOCUMENTS

| CN | 102128763 A | 7/2011 |
| CN | 102221511 A | 10/2011 |
| CN | 103471958 A | 12/2013 |
| CN | 103558115 A | 2/2014 |
| GB | 223951 A | 11/1924 |

\* cited by examiner

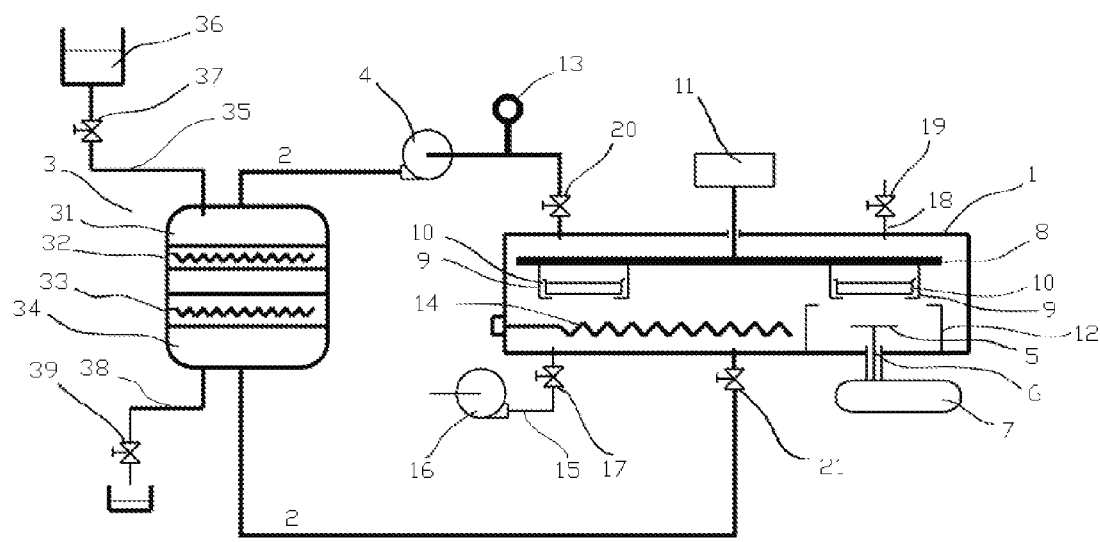

FULL-AUTOMATIC DYNAMIC TOBACCO MOISTURE ANALYSIS CLIMATE CHAMBER

CROSS REFERENCE TO RELATED PATENT APPLICATION

The present application is the US national stage of PCT/CN2014/084596 filed on Aug. 18, 2014, which claims the priority of the Chinese patent applications No. 201310442801.9 filed on Sep. 25, 2013, which applications are incorporated herein by reference.

BACKGROUND OF THE PRESENT INVENTION

1. Field of Invention

The present invention relates to a full-automatic dynamic tobacco moisture analysis climate chamber.

2. Description of Related Arts

Aroma-enhancement and moisture-retention of a cigarette is one of major science and technology projects of tobacco industry in the 12th Five-Year-Plan period. Moisture retention ability of the cigarette is a major influencing factor for cigarette quality. In the research process of the moisture retention of the cigarette, the first problem is how to accurately and conveniently test and evaluate the moisture retention ability. A conventional evaluation method of the moisture retention ability is placing a blank tobacco shred sample and a tobacco shred sample added with humectant in a desiccator or a constant-temperature constant-humidity chamber contained with saturated salt solution, sampling and weighing at regular time, obtaining moisture contents of the sample at each time by using Oven Method, and performing drawing and comparison. The above method has the following disadvantages: 1) the test period is relative long, the method is tedious, and the tobacco sample generally requires for 3-5 days for an unwetting equilibrium in such static measurement method, which requires for many and repetitive manual operations; 2) because the tobacco is a colloidal capillary cellular thin-layer material, and has relative strong moisture absorbability, the test result is susceptible to effects of operators and operating environment where the sample exposes, with the result of inaccurate results and poor repeatability; 3) only a few discontinuous data points are obtained, which fails to reflect subtle variations of the moisture contents of the tobacco sample over time, and is difficult to study kinetic rules of moisture dehydration or moisture absorption of tobacco shreds. In recent years, it has developed a dynamic moisture analysis system (DVS) for evaluating the moisture retention ability of the tobacco, which, however, fails to give extended application due to negative factors, e.g., the sample amount is small (which is less than 1 g), it is unable to realize simultaneous detection of multiple samples, etc. In view of the above reasons, it is of great significance to establish a new device to achieve a full-automatic, multiple samples, large sample amount and real-time online analysis of the moisture retention ability test of the tobacco.

SUMMARY OF THE PRESENT INVENTION

In view of the above disadvantages in the prior art, an object of the present invention is to provide a full-automatic dynamic tobacco moisture analysis climate chamber, to solve the problem of lacking a device to achieve a full-automatic, multiple samples, large sample amount and real-time online analysis of the moisture retention ability evaluation of the tobacco in the prior art.

In order to achieve the above object and other related objects, the present invention provides a full-automatic dynamic tobacco moisture analysis climate chamber, comprising an enclosed constant-temperature constant-humidity cabin, the constant-temperature constant-humidity cabin is communicated with an air temperature and humidity processor through two air delivery pipelines to form an air circulation loop, the air delivery pipeline is provided with a blower; a weighing platform is disposed inside the constant-temperature constant-humidity cabin, the weighing platform is connected to a weighing sensor of an electron balance via a straight tube that penetrates a housing of the constant-temperature constant-humidity cabin, the electron balance is located outside the constant-temperature constant-humidity cabin; a sample delivery hanger is hung inside the constant-temperature constant-humidity cabin, at least one placement carrier is disposed below the sample delivery hanger, a sample vessel is placed on the placement carrier, the sample delivery hanger is further connected to a drive mechanism outside the constant-temperature constant-humidity cabin and the drive mechanism drives the sample delivery hanger to perform operations, to place the sample vessel on the weighing platform for weighing.

Preferably, a lower surface of the placement carrier is provided with a bracket opening, which is larger than the maximum cross section of the weighing platform; the bracket opening is located below the sample vessel, the sample vessel is freely movable up and down in the placement carrier.

Preferably, the weighing platform is located inside an enclosed shell, the enclosed shell is provided with an enclosed shell opening facing an upper part of the weighing platform, and the enclosed shell opening is larger than the maximum cross section of the placement carrier; a lower surface of the sample delivery hanger is opposite to an upper surface of the enclosed shell, such that when the sample delivery hanger moves downwards to contact with the enclosed shell, the lower surface of the sample delivery hanger is sealed with the upper surface of the enclosed shell.

Preferably, the sample delivery hanger is a horizontal disc, which is movable up and down, and is rotatable around a circle center by the drive of a drive mechanism; the placement carriers are distributed circumferentially along the horizontal disc.

Preferably, the air delivery pipeline is further provided with a temperature and humidity sensor.

Preferably, a heater is disposed inside the constant-temperature constant-humidity cabin.

Preferably, the constant-temperature constant-humidity cabin is communicated with a fresh air blower through a blower pipeline, and the other end of the fresh air blower is located in outside air, the blower pipeline is provided with a first stop valve; the constant-temperature constant-humidity cabin is further communicated with the outside air though a moisture exhaust pipeline, and the moisture exhaust pipeline is provided with a second stop valve; the two air delivery pipelines are provided with a fifth stop valve and a sixth stop valve respectively at the end that closes to the constant-temperature constant-humidity cabin.

Preferably, the air temperature and humidity processor is successively arranged with a humidification unit, a heating unit, a cooling unit and a dehumidification unit along an air flow path; the humidification unit is communicated with a water feeding tank though a water feeding pipeline, the water feeding pipeline is provided with a third stop valve;

the dehumidification unit is communicated with outside air though a dehumidification pipeline, and the dehumidification pipeline is provided with a fourth stop valve.

From the above, the full-automatic dynamic tobacco moisture analysis climate chamber of the present invention has the following beneficial effects:

the full-automatic dynamic tobacco moisture analysis climate chamber, can minimize the test period, minimize intermediate links and human operation errors; the tobacco sample preparation in one process can obtain an equilibrium mass of the tobacco sample in a standard environment, a variation curve of a mass of the tobacco sample in a preset environment over time, and a mass of the tobacco sample after drying and dehydration and the like, so as to obtain a variation curve of the moisture content of the tobacco sample over time, and thus obtain the change rule of the moisture content of the tobacco sample as an important basis for performance evaluation of a tobacco humectant.

BRIEF DESCRIPTION OF THE DRAWINGS

FIG. 1 shows a structure diagram of a full-automatic dynamic tobacco moisture analysis climate chamber of the present invention.
Illustrations of Reference Numerals of Elements:
1 constant-temperature constant-humidity cabin
2 air delivery pipeline
3 air temperature and humidity processor
31 humidification unit
32 heating unit
33 cooling unit
34 dehumidification unit
35 water feeding pipeline
36 water feeding tank
37 third stop valve
38 dehumidification pipeline
39 fourth stop valve
4 blower
5 weighing platform
6 straight tube
7 electron balance
8 sample delivery hanger
9 placement carrier
10 sample vessel
11 drive mechanism
12 enclosed shell
13 temperature and humidity sensor
14 heater
15 blower pipeline
16 fresh air blower
17 first stop valve
18 moisture exhaust pipeline
19 second stop valve
20 fifth stop valve
21 sixth stop valve

DETAILED DESCRIPTION OF THE PREFERRED EMBODIMENTS

The embodiment modes of the present invention are described hereunder through specific examples, and persons skilled in the art may easily understand other advantages and efficacies of the present invention from the contents disclosed in the present description.

Please refer to FIG. 1. It should be known that the form, the scale, the size and the like shown in the drawings attached in this specification are all simply used to match with the content exposed by the specification for the skilled in the art understanding and reading, but not used to limit qualifications when the invention may be implemented. Meanwhile, terms such as "up", "down", "left", "right" and the like cited in this specification are also simply for clearness of the description but not used to limit the scope implemented by the invention. The change or the adjustment of the relative relation should also be seen as the scope of the invention when there is no substantial alteration in the technical content.

As shown in FIG. 1, the present invention provides a full-automatic dynamic tobacco moisture analysis climate chamber, which comprises an enclosed constant-temperature constant-humidity cabin 1, the constant-temperature constant-humidity cabin 1 is communicated with an air temperature and humidity processor 3 through two air delivery pipelines 2 to form an air circulation loop, the air delivery pipeline 2 is provided with a blower 4; a weighing platform 5 is disposed inside the constant-temperature constant-humidity cabin 1, the weighing platform 5 is connected to a weighing sensor of an electron balance 7 via a straight tube 6 that penetrates a housing of the constant-temperature constant-humidity cabin 1, the electron balance 7 is located outside the constant-temperature constant-humidity cabin 1; a sample delivery hanger 8 is hung inside the constant-temperature constant-humidity cabin 1, at least one placement carrier 9 is disposed below the sample delivery hanger 8, a sample vessel 10 is placed on the placement carrier 9, the sample delivery hanger 8 is further connected to a drive mechanism 11 outside the constant-temperature constant-humidity cabin 1, and the drive mechanism 11 drives the sample delivery hanger 8 to perform operations, to place the sample vessel 10 on the weighing platform 5 for weighing.

The air temperature and humidity processor 3 may adjust the air temperature and relative humidity, then the blower 4 carries out air circulation, to cause the air in the air temperature and humidity processor 3 to enter the constant-temperature constant-humidity cabin 1, thereby the constant-temperature constant-humidity cabin 1 keeps the temperature and relative humidity required in experiments.

Prior to performing the experiment, the air temperature and relative humidity are firstly adjusted by using the air temperature and humidity processor 3, to make the air temperature and relative humidity in the constant-temperature constant-humidity cabin 1 meet a standard value. Over time, the tobacco sample in the sample vessel 10 gradually achieves a moisture content equilibrium status in the constant-temperature constant-humidity cabin 1; during such process, the drive mechanism 11 drives the sample delivery hanger 8 to place the sample vessel 10 with the tobacco sample on the weighing platform 5 for weighing in accordance with a preset time interval. If a change in mass of the sample vessel 10 with the tobacco sample is relative small, generally 0.2%, then the tobacco sample may be considered to achieve the moisture content equilibrium status.

After the tobacco sample achieves the moisture content equilibrium status, it is able to perform the dynamic test of the moisture content of the tobacco sample by using the full-automatic dynamic tobacco moisture analysis climate chamber. At this point, the air temperature and relative humidity are adjusted by using the air temperature and humidity processor 3, to make the air temperature and relative humidity in the constant-temperature constant-humidity cabin 1 meet a preset value, generally, the precision of the air temperature in the constant-temperature constant-humidity cabin 1 is up to ±0.2° C. of the preset value, and the precision of the relative humidity is up to ±0.5% of the preset value. If the preset value of the relative humidity of the air in the constant-temperature constant-humidity cabin 1 is less than the current relative humidity in the constant-temperature constant-humidity cabin 1, then the dynamic test of the moisture content is a water dehydration test, whereas, if the preset value of the relative humidity of the air in the constant-temperature constant-humidity cabin 1 is larger than the current relative humidity in the constant-temperature constant-humidity cabin 1, then the dynamic test of the moisture content is a water absorption test.

In the process of the dynamic test of the moisture content, the drive mechanism 11 drives the sample delivery hanger 8 to place the sample vessel 10 with the tobacco sample on the weighing platform 5 for weighing in accordance with a preset time interval, till the change in mass of the sample vessel 10 with the tobacco sample is relative small, generally 0.2%, then it can be considered that the tobacco sample is in the moisture content equilibrium in the preset environment, and the test is ended, thereby the change curve of the mass of the tobacco sample over time in the preset environment is obtained.

Because that the space of the constant-temperature constant-humidity cabin 1 is a closed circulation, and the volume thereof is relative small, therefore, the adjustable precision is high, and the response time is short, which, as compared to the open circulation and the dehumidify by using a concentrated sulfuric acid and salt solution in the prior art, has better precision and security, small system inertia, and relative high level response speed.

There may be a plurality of placement carriers 9 as experimental required, as well as the tobacco samples in the sample vessel 10, by which it may test a plurality of tobacco samples at one time, resulting in saving experimental time, and facilitating the comparison among different tobacco samples in the meanwhile. In the case that a plurality of sample vessels is used, when weighing the mass of the tobacco sample, the drive mechanism 11 drives the sample delivery hanger 8 to successively place the sample vessels 10 with the tobacco sample on the weighing platform 5 for weighing in accordance with a preset time interval, and the electron balance 7 successively records the mass of the weighed sample vessels 10. After the completion of the weighs of all the sample vessels 10, the electron balance 7 is reset, and then it begins to perform the next round of weigh from the first sample vessel 10; the electron balance 7 is reset after each round of weigh, and the variation curve of the mass of the tobacco sample over time is obtained.

Prior to the experiment, it may calibrate the electron balance 7 by using a built-in weigh, which helps to effectively avoid the problems of system error and zero shift, so as to obtain more accurate data to reflect the subtle variations of the moisture content data.

A lower surface of the placement carrier 9 is provided with a bracket opening, which is larger than the maximum cross section of the weighing platform 5; the bracket opening is located below the sample vessel 10, the sample vessel 10 is freely movable up and down in the placement carrier 9.

As the sample delivery hanger 8 places the sample vessel 10 on the weighing platform 5, the weighing platform 5 lifts the sample vessel 10 through the bracket opening, to weigh the sample vessel 10. After weighing, the sample delivery hanger 8 lifts the placement carrier 9, and the sample vessel 10 leaves the weighing platform 5 together with the placement carrier 9. In such way, the placement carrier 9 is simple in design, and the weight of the sample vessel 10 is simple and feasible.

The weighing platform 5 is located inside an enclosed shell 12, the enclosed shell 12 is provided with an enclosed shell opening facing an upper part of the weighing platform 5, and the enclosed shell opening is larger than the maximum cross section of the placement carrier 9; a lower surface of the sample delivery hanger 8 is opposite to an upper surface of the enclosed shell 12, such that when the sample delivery hanger 8 moves downwards to contact with the enclosed shell 12, the lower surface of the sample delivery hanger 8 is sealed with the upper surface of the enclosed shell 12.

When the sample delivery hanger 8 places the sample vessel 10 on the weighing platform 5, the placement carrier 9 enter the enclosed shell 12 through the enclosed shell opening, while the sample delivery hanger 8 moves downwards to contact with the enclosed shell 12, the lower surface of the sample delivery hanger 8 is sealingly engaged with the upper surface of the enclosed shell 12, thereby blocking the circulating air flow in the constant-temperature constant-humidity cabin 1, and causing the enclosed shell 12 to form a small closed space. As weighing the tobacco sample in the small closed space, it enables to improve the accuracy of weighing.

The sample delivery hanger 8 is a horizontal disc, which is movable up and down and is rotatable around a circle center by the drive of the drive mechanism 11; the placement carriers 9 are distributed circumferentially along the horizontal disc. When the horizontal disc moves downwards, the placement carrier 9 brings the sample vessel 10 to move downwards and to be placed on the weighing platform 5 for weighing. For example, the sample delivery hanger 8 is disposed with a plurality of placement carriers 9, which are distributed circumferentially along the horizontal disc; after a sample vessel 10 is weighed, the horizontal disc lifts upwards, rotates a certain angle around the circle, then moves downwards, to weigh the next sample vessel 10. As such, the weighs of the plurality of tobacco samples are easily achieved. The sample delivery hanger 8 may further adopts a three-dimensional, i.e., X-Y-Z, mechanical arm, by which the sample vessels 10 are placed one by one on the weighing platform 5 for weighing.

The air delivery pipeline 2 is further provided with a temperature and humidity sensor 13. The temperature and humidity sensor 13 is used to real-time monitor the air temperature and relative humidity in the air delivery pipeline 2, so as to monitor the air temperature and relative humidity in the air circulation loop formed by the constant-temperature constant-humidity cabin 1 and the air temperature and humidity processor 3.

A heater 14 is disposed inside the constant-temperature constant-humidity cabin 1. The heater is used to heat the air in the constant-temperature constant-humidity cabin 1.

The constant-temperature constant-humidity cabin 1 is communicated with a fresh air blower 16 through a blower pipeline 15, and the other end of the fresh air blower 16 is located in outside air; the blower pipeline 16 is provided with a first stop valve 17; the constant-temperature constant-humidity cabin 1 is further communicated with the outside air though a moisture exhaust pipeline 18, and the moisture exhaust pipeline 18 is provided with a second stop valve 19; the two air delivery pipelines 2 are provided with a fifth stop valve 20 and a sixth stop valve 21 respectively at the end that closes to the constant-temperature constant-humidity cabin.

During the moisture test of the tobacco sample, it needs to shut down the air temperature and humidity processor 3, the blower 4, the fifth stop valve 20 and the sixth stop valve 21 that are connected to the constant-temperature constant-humidity cabin 1, and turn on the second stop valve 19, the fresh air blower 16 and the first stop valve 17 to dry the tobacco sample. As such, the constant-temperature constant-humidity cabin 1 turns into an oven, which is full-automatic operated. At this point, it may further turn on the heater 14 inside the constant-temperature constant-humidity cabin 1, heat and keep the air in the constant-temperature constant-humidity cabin 1 to a certain temperature; after a period of time, the drive mechanism 11 drives the sample delivery hanger 8 to place the sample vessel 10 with the tobacco sample on the weighing platform 5 for weighing, to obtain the mass of the tobacco sample after dying and water dehydration.

The air temperature and humidity processor 3 is successively arranged with a humidification unit 31, a heating unit 32, a cooling unit 33 and a dehumidification unit 34 along an air flow path; the humidification unit 31 is communicated with a water feeding tank 36 though a water feeding pipeline 35, the water feeding pipeline 35 is provided with a third stop valve 37; the dehumidification unit 34 is communicated with outside air though a dehumidification pipeline 38, and the dehumidification pipeline 38 is provided with a fourth stop valve 39. The humidification unit 31 is preferably spray humidification; the heating unit 32 is preferably an electric heater for heating; the cooling unit 33 is preferably a compressor heat exchanger for cooling; the dehumidification unit 34 is preferably condensation dehumidification, and is more preferably regenerative adsorption dehumidification.

A specific usage method of the above full-automatic dynamic tobacco moisture analysis climate chamber is used to draw a variation curve of the moisture content of the tobacco sample over time, with the detailed steps as below:

1) preparation of tobacco sample: preparing a tobacco sample according to YC/T31-1996, and placing the tobacco sample in the sample vessel 10 with known mass, then placing the sample vessel 10 on the placement carrier 9 disposed in the constant-temperature constant-humidity cabin 1, wherein there may place a series of sample vessels at the same time; 2) moisture content equilibrium of the tobacco sample in the standard environment: setting the air environment of the constant-temperature constant-humidity cabin 1 according to the ISO3402 standard, wherein the temperature is 22° C.±1° C., the relative humidity is 60% RH±2%, and more preferably, the temperature is 22° C.±0.2° C., and the relative humidity is 60% RH±0.5%; at this point, the heater 14, the second stop valve 19, the fresh air blower 16 and the first stop valve 17 are closed;

after the tobacco sample in the sample vessel 10 exposes to the above air environment for 48 hours, the drive mechanism 11 drives the sample delivery hanger 8 to successively place the sample vessel 10 with the tobacco sample on the weighing platform 5 for weighing, after the completion of weighing all the sample vessels 10, the electron balance 7 is reset, then it begins to perform the next round weigh from the first sample vessel 10, and cycles repeatedly, and records each weighing result in the meanwhile; generally, if the change in mass of the sample vessel 10 in three hours in is less than 0.2%, it may be considered that the mass is the equilibrium mass of the tobacco sample in the standard environment;

3) dynamic test of the moisture content: setting the temperature and the relative humidity of the air environment of the constant-temperature constant-humidity cabin 1 as preset values, wherein, the preset values may be set as multiple segment data, e.g., the air temperature is set as 22° C., the relative humidity is set as 40%; since the preset value of the humidity is less than that of the current humidity of the constant-temperature constant-humidity cabin 1, the result of the dynamic test of the moisture content is a water dehydration test; the blower 4 circles the air in the constant-temperature constant-humidity cabin 1 and the air in the air temperature and humidity processor 3, the air temperature and humidity processor 3 continually heats, humidifies, cools, dehumidifies the circled air, while the temperature and humidity sensor 13 performs real-time monitor to make the temperature of the circled air within a range of the preset value±0.2° C., and the relative humidity within a range of the preset value±0.5%;

the drive mechanism 11 drives the sample delivery hanger 8 to successively place the sample vessel 10 with the tobacco sample on the weighing platform 5 for weighing, after the completion of weighing all the sample vessels 10, the electron balance 7 is reset, and then it begins to perform the next round weigh from the first sample vessel 10, and cycles repeatedly, and records each weighing result in the meanwhile; generally, if the change in mass of the sample vessel 10 in three hours is less than 0.2%, then the mass may be considered as the equilibrium mass of the tobacco sample in the preset environment equilibrium; according to the mass of the tobacco samples weighed at different times, it may obtain the variation curve of the mass of the tobacco sample in the preset environment over time;

4) moisture test of the tobacco sample: shutting down the air temperature and humidity processor 3, the blower 4, the fifth stop valve 20 and the sixth stop valve 21 that are connected to the constant-temperature constant-humidity cabin 1, and turning on the second stop valve 19 to an opening of 33%, turning on the fresh air blower 16, turning on the first stop valve 17 to an opening of 25%, to dry the tobacco sample; at this point, the constant-temperature constant-humidity cabin 1 turns into an experimental oven that accords with the YC-T31-1996 standard, and the oven is full-automatic operated; turning on the heater 14 inside the constant-temperature constant-humidity cabin 1, heat and keep the air in the constant-temperature constant-humidity cabin 1 to a temperature of 100° C.±1° C.; after two hours, the drive mechanism 11 drives the sample delivery hanger 8 to successively place the sample vessel 10 with the tobacco sample on the weighing platform 5 for weighing, to obtain the mass of the tobacco sample after dying and water dehydration.

5) drawing the variation curve of the moisture content of the tobacco sample over time according to the above measured values.

It may also adopt another specific usage method of the above full-automatic dynamic tobacco moisture analysis climate chamber for isothermal moisture absorption-unwetting investigation:

weighing a tobacco shred sample of 1 g and placing it in each sample vessel 10 respectively, setting a pretreatment procedure, wherein the constant-temperature constant-humidity cabin 1 has a temperature of T=100° C. for 3 hours, to obtain dried tobacco shreds. Then setting a isothermal moisture absorption-unwetting environmental temperature, and the constant-temperature constant-humidity cabin 1 has a temperature of T=25° C. Wherein the humidifying procedure of the relative humidity in the constant-temperature constant-humidity cabin 1 is set as below: RH=0% $\xrightarrow{\Delta RH=20\%}$ RH=80% $\xrightarrow{\Delta RH=15\%}$ RH=95%; the drying procedure of the relative humidity in the constant-temperature constant-humidity cabin 1 is set as below: RH=95% $\xrightarrow{\Delta RH=-15\%}$ RH=80% $\xrightarrow{\Delta RH=-20\%}$ RH=0%; and the holding time for each gradient is set as t=6 hours. Finally, the variation curve of the moisture content of the tobacco shred sample over time is drawn.

From the above, the full-automatic dynamic tobacco moisture analysis climate chamber of the present invention can minimize the test period, minimize intermediate links and human operation errors; the tobacco sample preparation in one process can obtain an equilibrium mass of the tobacco sample in a standard environment, a variation curve of a mass of the tobacco sample in a preset environment over time, and a mass of the tobacco sample after drying and dehydration and the like, so as to obtain a variation curve of the moisture content of the tobacco sample over time, and thus obtain the change rule of the moisture content of the tobacco sample as an important basis for performance evaluation of a tobacco humectant. Therefore, the present invention effectively overcomes a variety of disadvantages in the prior art and has high industrial utility value.

The abovementioned embodiments only illustratively describe the principle and efficacy of the present invention, rather than being used to limit the present invention. Any person skilled in the art may modify or amend the abovementioned embodiments without departing from the spirit and scope of the present invention. Thus, all equivalent modifications or amendments accomplished by persons having common knowledge in the technical field concerned without departing from the spirit and technical thoughts revealed by the present invention shall still be covered by the claims of the present invention.

What is claimed is:

1. A full-automatic dynamic tobacco moisture analysis climate chamber, characterized in that, it comprises an enclosed constant-temperature constant-humidity cabin, the constant-temperature constant-humidity cabin is communicated with an air temperature and humidity processor through two air delivery pipelines to form an air circulation loop, the air delivery pipeline is provided with a blower; a weighing platform is disposed inside the constant-temperature constant-humidity cabin, the weighing platform is connected to a weighing sensor of an electron balance via a straight tube that penetrates a housing of the constant-temperature constant-humidity cabin, the electron balance is located outside the constant-temperature constant-humidity cabin; a sample delivery hanger is hung inside the constant-temperature constant-humidity cabin, at least one placement carrier is disposed below the sample delivery hanger, a sample vessel is placed on the placement carrier, the sample delivery hanger is further connected to a drive mechanism outside the constant-temperature constant-humidity cabin, and the drive mechanism drives the sample delivery hanger to perform operations, to place the sample vessel on the weighing platform for weighing, a lower surface of the placement carrier is provided with a bracket opening, which is larger than the maximum cross section of the weighing platform; the bracket opening is located below the sample vessel, the sample vessel is freely movable up and down in the placement carrier.

2. The full-automatic dynamic tobacco moisture analysis climate chamber according to claim 1, characterized in that, the weighing platform is located inside an enclosed shell, the enclosed shell is provided with an enclosed shell opening facing an upper part of the weighing platform, and the enclosed shell opening is larger than the maximum cross section of the placement carrier; a lower surface of the sample delivery hanger is opposite to an upper surface of the enclosed shell, such that as the sample delivery hanger moves downwards to contact with the enclosed shell, the lower surface of the sample delivery hanger is sealingly engaged with the upper surface of the enclosed shell.

3. The full-automatic dynamic tobacco moisture analysis climate chamber according to claims 1, characterized in that, the sample delivery hanger is a horizontal disc, which is movable up and down and is rotatable about a circle center by the drive of the drive mechanism; the placement carriers are distributed circumferentially along the horizontal disc.

4. The full-automatic dynamic tobacco moisture analysis climate chamber according to claim 1, characterized in that, the air delivery pipeline is further provided with a temperature and humidity sensor.

5. The full-automatic dynamic tobacco moisture analysis climate chamber according to claim 1, characterized in that, a heater is disposed inside the constant-temperature constant-humidity cabin.

6. The full-automatic dynamic tobacco moisture analysis climate chamber according to claim 1, characterized in that, the constant-temperature constant-humidity cabin is communicated with a fresh air blower through a blower pipeline, and the other end of the fresh air blower is located in outside air, the blower pipeline is provided with a first stop valve; the constant-temperature constant-humidity cabin is further communicated with the outside air though a moisture exhaust pipeline, and the moisture exhaust pipeline is provided with a second stop valve; the two air delivery pipelines are provided with a fifth stop valve and a sixth stop valve respectively at the ends that close to the constant-temperature constant-humidity cabin.

7. The full-automatic dynamic tobacco moisture analysis climate chamber according to claim 1, characterized in that, the air temperature and humidity processor is successively arranged with a humidification unit, a heating unit, a cooling unit and a dehumidification unit along an air flow path; the humidification unit is communicated with a water feeding tank though a water feeding pipeline, the water feeding pipeline is provided with a third stop valve; the dehumidification unit is communicated with outside air though a dehumidification pipeline, and the dehumidification pipeline is provided with a fourth stop valve.

8. The full-automatic dynamic tobacco moisture analysis climate chamber according to claim 5, characterized in that, the constant-temperature constant-humidity cabin is communicated with a fresh air blower through a blower pipeline, and the other end of the fresh air blower is located in outside air, the blower pipeline is provided with a first stop valve; the constant-temperature constant-humidity cabin is further communicated with the outside air though a moisture exhaust pipeline, and the moisture exhaust pipeline is provided with a second stop valve; the two air delivery pipelines are provided with a fifth stop valve and a sixth stop valve respectively at the ends that close to the constant-temperature constant-humidity cabin.

* * * * *